United States Patent [19]

Kluth et al.

[11] Patent Number: 5,525,579
[45] Date of Patent: Jun. 11, 1996

[54] SUBSTITUTED TRIAZOLINONES

[75] Inventors: Joachim Kluth, Langenfeld; Klaus-Helmut Müller, Düsseldorf; Wilhelm Haas, Pulheim; Karl-Heinz Linker; Kurt Findeisen, both of Leverkusen; Klaus König, Odenthal; Hans-Joachim Santel; Markus Dollinger, both of Leverkusen, all of Germany

[73] Assignee: Bayer Aktiengesellschaft, Leverkusen, Germany

[21] Appl. No.: 241,091

[22] Filed: May 10, 1994

[30] Foreign Application Priority Data

May 17, 1993 [DE] Germany .............. 43 16 430.7

[51] Int. Cl.⁶ .............. A01N 43/653; C07D 249/12
[52] U.S. Cl. .............. 504/273; 548/263.4
[58] Field of Search .............. 548/263.4; 504/273

[56] References Cited

U.S. PATENT DOCUMENTS

| | | |
|---|---|---|
| 5,021,080 | 6/1991 | Muller et al. .............. 548/263.4 |
| 5,356,865 | 10/1994 | Muller et al. .............. 548/263.4 |
| 5,378,681 | 1/1995 | Schollner et al. .............. 548/263.4 |

OTHER PUBLICATIONS

Patent Abstracts of Japan, Week 4198, C77, vol. 2, Feb. 16, 1978, one page; "Triazoline derivatives, method of preparing the same, and herbicides", Nippon Soda KK, T. Okabe.

*Primary Examiner*—Patricia L. Morris
*Attorney, Agent, or Firm*—Sprung Horn Kramer & Woods

[57] ABSTRACT

The invention relates to new substituted triazolinones of the general formula (I)

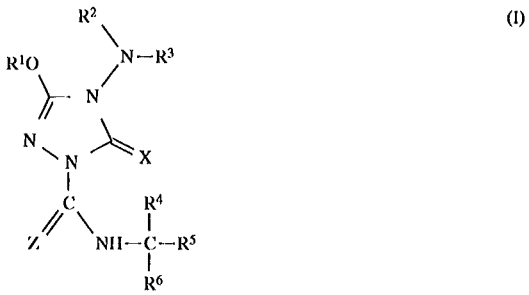

in which $R^1$ represents alkyl, halogenoalkyl, alkoxyalkyl or cycloalkyl, $R^2$ and $R^1$ either independently of one another in each case represent hydrogen, alkyl or alkoxycarbonyl, or together with the nitrogen atom to which they are bonded represent an optionally substituted alkylideneimino radical, $R^4$ either represents hydrogen, cyano, alkyl, alkenyl, alkinyl or halogenoalkyl and $R^5$ represents hydrogen, alkyl or halogenoalkyl, or $R^4$ and $R^5$ together with the carbon atom to which they are bonded represent cycloalkyl, $R^6$ represents hydrogen or in each case optionally substituted alkyl, cycloalkyl, aryl, arylalkyl or heteroaryl, X represents oxygen or sulphur and Z represents oxygen or sulphur, to a plurality of processes for their preparation, to a plurality of new intermediates, and to their use as herbicides.

7 Claims, No Drawings

SUBSTITUTED TRIAZOLINONES

The invention relates to new substituted triazolinones, to a plurality of processes for their preparation, to a plurality of new intermediates, and to their use as herbicides.

It has been disclosed that certain substituted triazolinones, such as, for example, the compound 3-methylthio-4-amino-1-[N-(1,1-dimethylethyl)-aminocarbonyl]-1,2,4-triazolin-5-one, have herbicidal properties (cf., for example, EP 391,187).

However, the herbicidal activity of these previously known compounds against problem weeds and their tolerance by important crop plants are not entirely satisfactory in all fields of application.

New substituted triazolinones of the general formula (I)

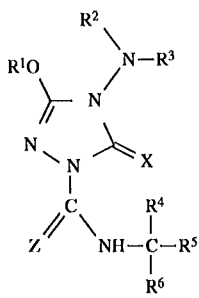

(I)

in which

R¹ represents alkyl, halogenoalkyl, alkoxyalkyl or cycloalkyl,

R² and R³ either independently of one another in each case represent hydrogen, alkyl or alkoxycarbonyl, or together with the nitrogen atom to which they are bonded represent an optionally substituted alkylidene-imino radical, R⁴ either represents hydrogen, cyano, alkyl, alkenyl, alkinyl or halogenoalkyl and R⁵ represents hydrogen, alkyl or halogenoalkyl, or R⁴ and R⁵ together with the carbon atom to which they are bonded represent cycloalkyl, R⁶ represents hydrogen or in each case optionally substituted alkyl, cycloalkyl, aryl, arylalkyl or heteroaryl, X represents oxygen or sulphur and Z represents oxygen or sulphur, have now been found.

The compounds of the formula (I) may exist in the form of optical isomers or isomer mixtures of various compositions, depending on the nature of the substituents. The invention claims the pure isomers and the isomer mixtures.

Furthermore, it has been found that the new substituted triazolinones of the general formula (I),

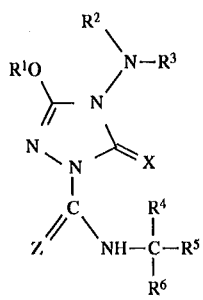

(I)

in which

R¹ represents alkyl, halogenoalkyl, alkoxyalkyl or cycloalkyl,

R² and R³ either independently of one another in each case represent hydrogen, alkyl or alkoxycarbonyl, or together with the nitrogen atom to which they are bonded represent an optionally substituted alkylidene-imino radical, R⁴ either represents hydrogen, cyano, alkyl, alkenyl, alkinyl or halogenoalkyl and R⁵ represents hydrogen, alkyl or halogenoalkyl, or R⁴ and R⁵ together with the carbon atom to which they are bonded represent cycloalkyl, R⁶ represents hydrogen or in each case optionally substituted alkyl, aryl or heteroaryl, X represents oxygen or sulphur and Z represents oxygen or sulphur, are obtained when a) activated (thio) carbonyltriazolinones of the formula (II)

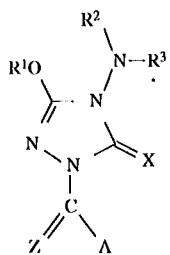

(II)

in which

R¹, R², R³, X and Z have the abovementioned meanings and

A represents an activating group, are reacted with amines of the formula (III)

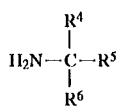

(III)

in which

R⁴, R⁵ and R⁶ have the abovementioned meanings, if appropriate in the presence of a diluent and if appropriate in the presence of a reaction auxiliary, or when b) triazolinones which are unsubstituted in the 1-position and have the formula (IV)

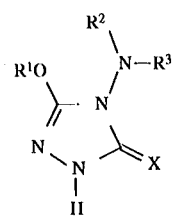

(IV)

in which

R¹, R², R³ and X have the abovementioned meanings, are reacted with iso(thio) cyanates of the formula (V)

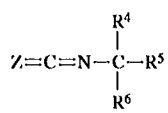

(V)

in which

R⁴, R⁵, R⁶ and Z have the abovementioned meanings, if appropriate in the presence of a diluent and if appropriate in the presence of a reaction auxiliary, or when c) substituted triazolinones of the formula (Ia)

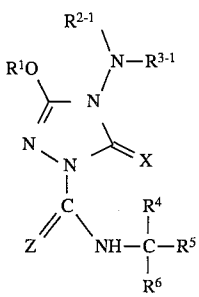

in which
R$^1$, R$^4$, R$^5$, R$^6$, X and Z have the abovementioned meanings and
R$^{2-1}$ and R$^{3-1}$ together with the nitrogen atom to which they are bonded represent an optionally substituted alkylideneimino radical, are reacted with acid, if appropriate in the presence of a diluent and if appropriate in the presence of a reaction auxiliary, or when d) substituted triazolinones of the formula (Ib)

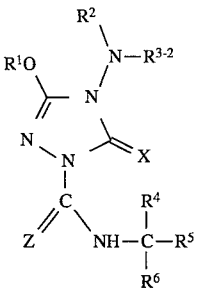

in which
R$^1$, R$^2$, R$^4$, R$^5$, R$^6$, X and Z have the abovementioned meanings and
R$^{3-2}$ represents alkoxycarbonyl, are hydrolysed, if appropriate in the presence of a diluent and if appropriate in the presence of a reaction auxiliary, and subsequently subjected to thermal decarboxylation.

Finally, it has been found that the new substituted triazolinones of the general formula (I) have herbicidal properties.

Surprisingly, the substituted triazilinones of the general formula (I) according to the invention have a considerably better herbicidal activity against problem weeds combined with a similarly good tolerance by important crop plants compared with the substituted triazolinones known from the prior art, such as, for example, the compound 3-methylthio-4-amino-1-[N-(t-butyl)-aminocarbonyl]- 1,2,4-triazolin-5-one, which are similar compounds chemically and from the point of view of action.

Formula (I) provides a general definition of the substituted triazolinones according to the invention. Preferred compounds of the formula (I) are those in which R$^1$ represents straight-chain or branched alkyl having 1 to 8 carbon atoms, straight-chain or branched halogenoalkyl having 1 to 8 carbon atoms and 1 to 17 identical or different halogen atoms, straight-chain or branched alkoxyalkyl having in each case 1 to 6 carbon atoms in the individual alkyl moieties, or cycloalkyl having 3 to 8 carbon atoms, R$^2$ and R$^3$ either independently of one another in each case represent hydrogen, straight-chain or branched alkyl having 1 to 8 carbon atoms or straight-chain or branched alkoxycarbonyl having 1 to 8 carbon atoms, or, together with the nitrogen atom to which they are bonded, represent a straight-chain or branched alkylideneimino radical having 1 to 8 carbon atoms, or a benzylideneimino radical which is optionally monosubstituted or polysubstituted by identical or different substituents, suitable substituents in the aryl moiety being: halogen, cyano, nitro, in each case straight-chain or branched alkyl, alkoxy, alkylthio, alkylsulphinyl or alkylsulphonyl, each of which has 1 to 6 carbon atoms, or in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, R$^4$ represents hydrogen, cyano, straight-chain or branched alkyl having 1 to 8 carbon atoms, straight-chain or branched alkenyl having 2 to 8 carbon atoms, straight-chain or branched alkinyl having 2 to 8 carbon atoms or straight-chain or branched halogenoalkyl having 1 to 8 carbon atoms and 1 to 17 identical or different halogen atoms and R$^5$ represents hydrogen, straight-chain or branched alkyl having 1 to 8 carbon atoms or straight-chain or branched halogenoalkyl having 1 to 8 carbon atoms and 1 to 17 identical or different halogen atoms, or R$^4$ and R$^5$ together with the carbon atom to which they are bonded represent cycloalkyl having 3 to 8 carbon atoms, R$^6$ represents hydrogen or straight-chain or branched alkyl which has 1 to 12 carbon atoms and is optionally monosubstituted or polysubstituted by identical or different substituents, suitable substituents being: halogen, cyano, cycloalkyl having 3 to 8 carbon atoms or aryl, aryloxy, arylthio or arylamino, each of which has 6 to 10 carbon atoms in the aryl moiety and each of which is optionally monosubstituted or polysubstituted by identical or different substituents, heteroaryl, heteroaryloxy, heteroarylthio or heteroarylamino, each of which has 1 to 9 carbon atoms and 1 to 4 identical or different hetero atoms—in particular nitrogen, oxygen and/or sulphur—in the heteroaryl moiety and each of which is substituted by identical or different substituents, suitable aryl or heteroaryl substituents in each case being: halogen, cyano, nitro, in each case straight-chain or branched alkyl, alkoxy, alkylthio, alkylsulphinyl or alkylsulphonyl, each of which has 1 to 6 carbon atoms, or in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms;

R$^6$ furthermore represents C$_3$–C$_8$-cycloalkyl or C$_6$- or C$_{10}$-aryl-C$_1$–C$_4$-alkyl each of which is optionally substituted by halogen or C$_1$–C$_4$-alkyl, R$^6$ furthermore represents aryl having 6 to 10 carbon atoms or heteroaryl having 1 to 9 carbon atoms and 1 to 4 identical or different hetero atoms—in particular nitrogen, oxygen and/or sulphur—, each of these aryl or heteroaryl radicals optionally being monosubstituted or polysubstituted by identical or different substituents, suitable aryl or heteroaryl substituents in each case being: halogen, cyano, nitro, in each case straight-chain or branched alkyl, alkoxy, alkylthio, alkylsulphinyl or alkylsulphonyl, each of which has 1 to 6 carbon atoms, or in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, X represents oxygen and sulphur and
Z represents oxygen and sulphur.

Particularly preferred compounds of formula (I) are those in which

R$^1$ represents straight-chain or branched alkyl having 1 to 6 carbon atoms, straight-chain or branched halogenoalkyl having 1 to 4 carbon atoms and 1 to 9 identical or different halogen atoms—in particular fluorine, chlorine and/or bromine—, straight-chain or branched alkoxyalkyl having in each case 1 to 4 carbon atoms in the individual alkyl moieties, or cycloalkyl having 3 to 7 carbon atoms, $R^2$ and $R^3$ either independently of one another in each case represent hydrogen, straight-chain or branched alkyl having 1 to 6 carbon atoms or straight-chain or branched alkoxycarbonyl having 1 to 6 carbon atoms, or, together with the nitrogen atom to which they are bonded, represent a straight-chain or branched alkylidencimino radical having 1 to 8 carbon atoms or a benzylidencimino radical which is optionally monosubstituted to trisubstituted by identical or different substituents, suitable substituents in the aryl moiety being: fluorine, chlorine, bromine, iodine, cyano, nitro, in each case straight-chain or branched alkyl, alkoxy, alkylthio, alkylsulphinyl or alkylsulphonyl, each of which has 1 to 4 carbon atoms, or in each case straight-chain or branched halogenoalkyl, halogenoalkoxy, halogenoalkylthio, halogenoalkylsulphinyl or halogenoalkylsulphonyl, each of which has 1 to 4 carbon atoms and 1 to 9 identical or different halogen atoms—in particular fluorine, chlorine and/or bromine—, $R^4$ either represents hydrogen, cyano, straight-chain or branched alkyl having 1 to 7 carbon atoms, straight-chain or branched alkenyl having 2 to 7 carbon atoms, straight-chain or branched alkinyl having 2 to 6 carbon atoms or straight-chain or branched halogenoalkyl having 1 to 6 carbon atoms and 1 to 13 identical or different halogen atoms—in particular fluorine, chlorine and/or bromine—and $R^5$ represents hydrogen, straight-chain or branched alkyl having 1 to 7 carbon atoms or straight-chain or branched halogenoalkyl having 1 to 6 carbon atoms and 1 to 13 identical or different halogen atoms—in particular fluorine, chlorine and/or bromine—or $R^4$ and $R^5$ together with the carbon atom with which they are bonded represent cycloalkyl having 3 to 7 carbon atoms, $R^6$ represents hydrogen or straight-chain or branched alkyl having 1 to 8 carbon atoms which is optionally monosubstituted to pentasubstituted by identical or different substituents, suitable substituents being: halogen—in particular fluorine, chlorine and/or bromine—, cyano, cycloalkyl having 3 to 7 carbon atoms, or phenyl, phenoxy, phenylthio or phenylamino, each of which is optionally monosubstituted to pentasubstituted by identical or different substituents, heteroaryl, heteroaryloxy, heteroarylthio or heteroarylamino, each of which has 1 to 9 carbon atoms and 1 to 3 identical or different hereto atoms—in particular nitrogen, oxygen and/or sulphur—in the heteroaryl moiety, each of which is monosubstituted to pentasubstituted by identical or different substituents, suitable phenyl or heteroaryl substituents in &ach case being: fluorine, chlorine, bromine, iodine, cyano, nitro, in each case straight-chain or branched alkyl, alkoxy, alkylthio, alkylsulphinyl or alkylsulphonyl, each of which has 1 to 4 carbon atoms, or in each case straight-chain or branched halogenoalkyl, halogenoalkoxy, halogenoalkylthio, halogenoalkylsulphinyl or halogenosulphonyl, each of which has 1 to 4 carbon atoms and 1 to 9 identical or different halogen atoms;

$R^6$ furthermore represents cyclohexyl or benzyl, $R^6$ furthermore represents phenyl or heteroaryl having 1 to 9 carbon atoms and 1 to 3 identical or different hetero atoms—in particular nitrogen, oxygen and/or sulphur—, each of these phenyl or heteroaryl radicals optionally being monosubstituted to pentasubstituted by identical or different substituents, suitable aryl or heteroaryl substituents in each case being: fluorine, chlorine, bromine, iodine, cyano, nitro, in each case straight-chain or branched alkyl, alkoxy, alkylthio, alkylsulphinyl or alkylsulphonyl, each of which has 1 to 4 carbon atoms, or in each case straight-chain or branched halogenoalkyl, halogenoalkoxy, halogenoalkylthio, halogenoalkylsulphinyl or halogenosulphonyl, each of which has 1 to 4 carbon atoms and 1 to 9 identical or different halogen atoms, X represents oxygen and sulphur and Z represents oxygen and sulphur.

Very particularly preferred compounds of the formula (I) are those in which $R^1$ represents methyl, ethyl, n- or i-propyl, n-, i-, s- or t-butyl, halogenoalkyl having 1 or 2 carbon atoms and 1 to 5 identical or different halogen atoms—in particular fluorine, chlorine and/or bromine—, or methoxymethyl, methoxyethyl, cyclopropyl or cyclohexyl, $R^2$ and $R^3$ either independently of one another in each case represent hydrogen, methyl, ethyl, n- or i-propyl, methoxycarbonyl or ethoxycarbonyl, or, together with the nitrogen atom to which they are bonded, represent a straight-chain or branched alkylidencimino radical having 1 to 6 carbon atoms or a benzylidencimino radical which is optionally monosubstituted to trisubstituted by identical or different substituents, suitable substituents in the aryl moiety being: fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, methylsulphonyl, trifluoromethyl, difluoromethyl, trifluoromethoxy, difluromethoxy, trifluoromethylthio, trifluoromethylsulphinyl, trifluromethylsulphonyl, $R^4$ either represents hydrogen, cyano, methyl, ethyl, n- or i-propyl, n-, i-, s- or t-butyl, allyl, propargyl or straight-chain or branched halogenoalkyl having 1 to 6 carbon atoms and 1 to 13 identical or different halogen atoms—in particular fluorine, chlorine and/or bromine—and $R^5$ represents hydrogen, methyl, ethyl, n- or i -propyl, n-, i-, s- or t-butyl or straight-chain or branched halogenoalkyl having 1 to 6 carbon atoms and 1 to 13 identical or different halogen atoms—in particular fluorine, chlorine and/or bromine—or $R^4$ and $R^5$ together with the carbon atom to which they are bonded represent cycloalkyl having 3 to 6 carbon atoms, $R^6$ represents hydrogen or straight-chain or branched alkyl having 1 to 7 carbon atoms which is optionally monosubstituted to trisubstituted by identical or different substituents, suitable substituents being: halogen—in particular fluorine, chlorine and/or bromine—, cyano, cycloalkyl having 3 to 6 carbon atoms, or phenyl, phenoxy, phenylthio or phenylamino, each of which is optionally monosubstituted to trisubstituted by identical or different substituents, or heteroaryl, heteroaryloxy, heteroarylthio or heteroarylamino, each of which has 1 to 5 carbon atoms and 1 to 3 identical or different hetero atoms—in particular nitrogen, oxygen and/or sulphur—in the heteroaryl moiety, and each of which is optionally monosubstituted to trisubstituted by identical for different substituents, suitable phenyl or heteroaryl substituents in each case being: fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, methylsulphonyl, trifluoromethyl, difluoromethyl, trifluoromethoxy, difluoromethoxy, trifluoromethylthio, trifluoromethylsulphinyl, trifluoromethylsulphonyl, $R^6$ furthermore represents phenyl or heteroaryl having 1 to 5 carbon atoms and 1 to 3 identical or different hetero atoms—in particular nitrogen, oxygen and/or sulphur,— each of these phenyl or heteroaryl radicals optionally being monosubstituted to trisubstituted by identical or different substituents, suitable aryl or heteroaryl substituents in each case being: fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, methylsulphonyl, trifluoromethyl, difluoromethyl, trifluoromethoxy, difluoromethoxy, trifluoromethylthio, trifluoromethylsulphinyl, trifluoromethylsulphonyl, X represents oxygen and sulphur and
Z represents oxygen and sulphur.

The following substituted triazolinones of the general formula (I) may be mentioned individually in addition to the compounds given in the preparation examples:

(I)

| $R^1$ | $R^2$ | $R^3$ | $R^4$ | $R^5$ | $R^6$ | X | Z |
|---|---|---|---|---|---|---|---|
| $CH_3$ | H | H | $CH_3$ | $-CH_2F$ | $-CH_2-F$ | O | O |
| $CH_3$ | H | H | $CH_3$ | $CH_3$ | $t-C_4H_9$ | O | O |
| $CH_3$ | H | $CH_3$ | $CH_3$ | H | ⌬-F | O | O |
| $CH_3$ | H | $CH_3$ | $CH_3$ | $CH_3$ | $-CH_2-O-C_6H_5$ | O | O |
| $CH_3$ | H | $C_2H_5$ | $CH_3$ | CN | $C_6H_5$ | O | |
| $CH_3$ | H | $CH_3$ | $C_2H_5$ | H | $C_6H_5$ | O | O |
| $CH_3$ | H | $CH_3$ | $CH_3$ | $CH_3$ | $C_2H_5$ | O | O |
| $C_2H_5$ | H | H | $CH_3$ | $CH_3$ | $-CH_2-Cl$ | O | O |
| $C_2H_5$ | H | $C_2H_5$ | $CH_3$ | $-CH_2-CH_2-CH_2-CH_2-CH_2-$ | | O | O |
| $C_2H_5$ | H | H | $CH_3$ | $CH_3$ | $-CH_2-CH_2-C_6H_5$ | O | O |
| $C_2H_5$ | H | $CH_3$ | $CH_3$ | $CH_3$ | $i-C_3H_7$ | O | O |
| $C_2H_5$ | H | $CH_3$ | $CH_3$ | H | isoxazole-$CH(CH_3)_2$ | O | O |
| $C_2H_5$ | H | $CH_3$ | H | H | $C_6H_5$ | O | O |

If, for example, 1-chlorocarbonyl-3-methoxy-4-isopropylideneimino-1,2,4-triazolin-5-one and t-butylamine are used as starting substances, the course of the reaction of process (a) according to the invention can be represented by the following equation:

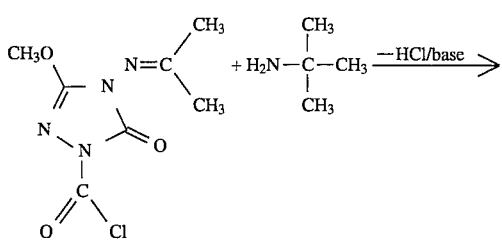

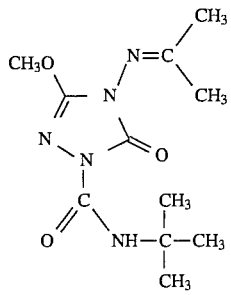

If, for example, 3-ethoxy-4-amino-1,2,4-triazolin-5-one and chloro-t-butyl isocyanate are used as starting substances, the course of the reaction of process (b) according to the invention can be represented by the following equation:

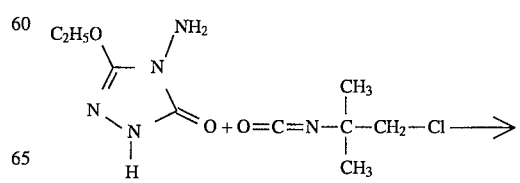

-continued

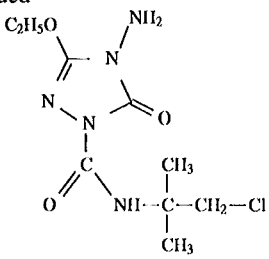

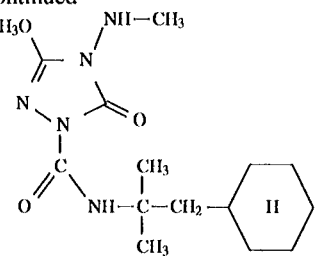

If, for example, 1-[N-(1-methyl-4-phenyl-but-2-yl)-amino]-carbonyl-3-n-propoxy-4-(4-methylpent-2-ylideneimino)-1,2,4-triazolin-5-one is used as starting compound, the course of the reaction of process (c) according to the invention can be represented by the following equation:

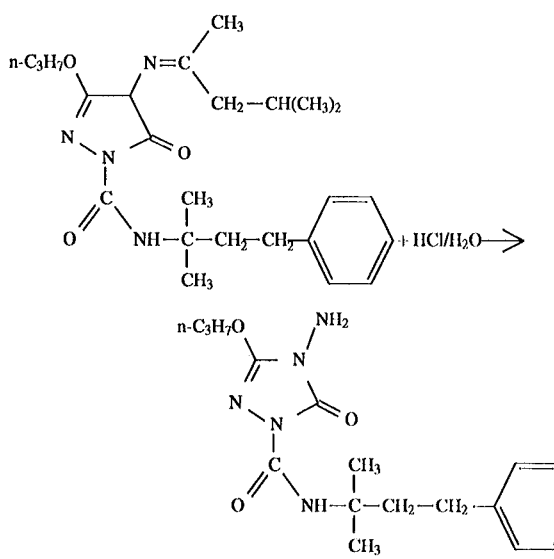

If, for example, 1-(N-2-methyl-3-cyclohexylprop-2-yl-amino)-carbonyl- 3-methoxy-4-(N-methyl-N-ethoxycarbonylamino)- 1,2,4-triazolin-5-one is used as starting compound, the course of the reaction process (d) according to the invention can be represented by the following equation:

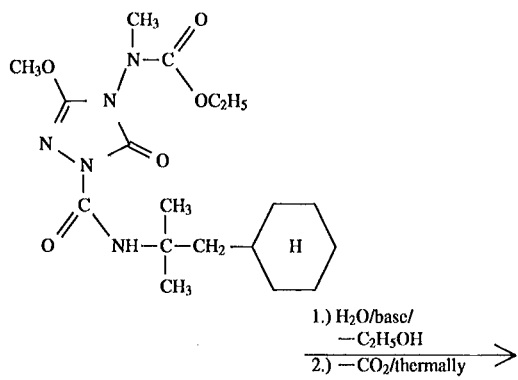

Formula (II) provides a general definition of the activated (thio) carbonyltriazolinones required as starting substances for carrying out process (a) according to the invention. In this formula (II), $R^1$, $R^2$, $R^3$, X and Z preferably represent those radicals which have already been mentioned in connection with the description of the compounds of the formula (I) according to the invention as being preferred for these substituents. A represents a customary radical which activates the adjacent carbonyl group, in particular chlorine, phenoxy or 1-imidazolyl.

The activated (thio)carbonyltriazolinones of the formula (II) were hitherto unknown and are also a subject of the invention. They are obtained, for example, when triazolinones which are unsubstituted in the 1-position, of the formula (IV)

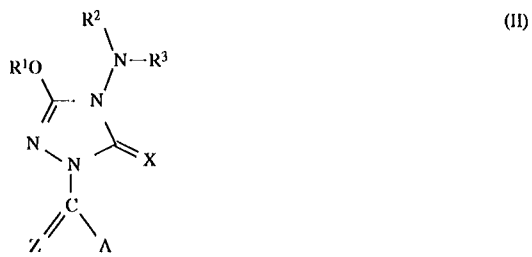

in which $R^1$, $R^2$, $R^3$, X and Z have the abovementioned meanings and

A represents an activating group, are reacted with (thio)phosgene or with phenyl (thio)chloroformate or with N,N'-carbonyldiimidazole at temperatures between −20° C. and +120° C., if appropriate in the presence of a diluent, such as, for example, chloroform and if appropriate in the presence of a reaction auxiliary, such as, for example, triethylamine.

Formula (III) provides a general definition of the amines furthermore required as starting substances for carrying out process (a) according to the invention. In this formula (III), $R^4$, $R^5$ and $R^6$ preferably represent those radicals which have already been mentioned in connection with the description of the compounds of the formula (I) according to the invention as being preferred for these substituents.

The amines of the formula (III) are generally known compounds of organic chemistry or can be obtained in analogy to generally known processes.

Formula (IV) provides a general definition of the triazolinones which are unsubstituted in the 1-position and which are required as educts for carrying out process (b) according to the invention and for the synthesis of the precursors of the formula (II). In this formula (IV), $R^1$, $R^2$, $R^3$ and X preferably represent those radicals which have already been mentioned in connection with the description of substances of the formula (I) according to the invention as being preferred for these substituents.

Some of the triazolinones of the formula (IV) which are unsubstituted in the 1-position are known (compare, for example, EP 442,469; J. Chem. Soc. C, 1967, 2700–2704; Arm. Khim. Zh. 29, 545–547 [1976] or CA 85:159998h).

Triazolinones which are unsubstituted in the 1-position, of the general formula (IVa)

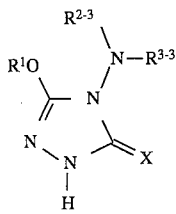

(IVa)

in which
R$^1$ and X have the abovementioned meanings and
R$^{2-3}$ either represents hydrogen, alkyl or alkoxycarbonyl and
R$^{3-3}$ represents alkyl or alkoxycarbonyl or
R$^{2-3}$ and R$^{3-3}$ together with the nitrogen atom to which they are bonded represent an optionally substituted alkylideneimino radical,
were hitherto unknown and are also a subject of the invention.

In this formula (IVa), the radicals R$^1$, X, R$^{2-3}$ and R$^{3-3}$ preferably represent those radicals which have already been mentioned above in connection with the description of the substances of the formula (I) according to the invention as being preferred for these substituents.

Known and hitherto unknown substituted triazolinones of the formula (IV), which are unsubstituted in the 1-position, are obtained in analogy to known processes (compare, for example, EP 422,469; J. Chem. Soc. C, 1967, 2700–2704; Arm. Khim. Zh. 29, 545–547 [1976] or CA 85:159998h), for example when (thio) carbodihydrazides of the formula (VI)

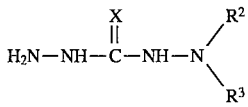

(VI)

in which
R$^2$, R$^3$ and X have the abovementioned meanings, are reacted with orthocarbonates of the formula (VII)

C(OR$^1$)$_4$ (VII), in which
R$^4$ has the abovementioned meaning, at temperatures between 0° C. and 120° C., if appropriate in the presence of a diluent, such as, for example, methanol or ethanol.

(Thio)carbodihydrazides of the formula (VI) and orthoesters of the formula (VII) are generally known compounds of organic chemistry or can be obtained with the aid of generally known processes.

Formula (V) provides a general definition of the iso(thio) cyanates furthermore required as educts for carrying out process (b) according to the invention. In this formula (V), R$^4$, R$^5$, R$^6$ and Z preferably represent those radicals which have already been mentioned in connection with the description of the substances of the formula (I) according to the invention as being preferred for these substituents.

The iso(thio) cyanates of the formula (V) are generally known compounds of organic chemistry or can be obtained in analogy to generally known processes.

Formula (Ia) provides a general definition of the substituted triazolinones required as educts for carrying out process (c) according to the invention. In this formula (Ia), R$^1$, R$^4$, R$^5$, R$^6$, X and Z preferably represent those radicals which have already been mentioned in connection with the description of the substances of the formula (I) according to the invention as being preferred for these substituents. R$^{2-1}$ and R$^{3-1}$ together with the nitrogen atom to which they are bonded preferably represent a straight-chain or branched alkylideneimino radical having 1 to 8 carbon atoms or a benzylideneimino radical which is optionally monosubstituted or polysubstituted by identical or different substituents, suitable substituents in the aryl moiety being: halogen, cyano, nitro, in each case straight-chain or branched alkyl, alkoxy, alkylthio, alkylsulphinyl or alkylsulphonyl, each of which has 1 to 6 carbon atoms, or in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms.

The substituted triazolinones of the formula (Ia) are compounds according to the invention and can be obtained with the aid of process (a) or (b) according to the invention.

Formula (Ib) provides a general definition of the substituted triazolinones which are required as educts for carryiny out process (d) according to the invention. In this formula (Ib), R$^1$, R$^2$, R$^4$, R$^5$, R$^6$, X and Z preferably represent those radicals which have already been mentioned in connection with the description of the substances of the formula (I) according to the invention as being preferred for these substituents. R$^{3-2}$ preferably represents straight-chain or branched alkoxycarbonyl having 1 to 8, in particular 1 to 6, carbon atoms.

The substituted triazolinones of the formula (Ib) are compounds according to the invention and can be obtained with the aid of process (a) or (b) according to the invention.

Suitable diluents for carrying out process (a) according to the invention are inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, methyl t-butyl ether, methyl t-pentyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, or bases, such as pyridine.

Process (a) according to the invention is preferably carried out in the presence of a suitable reaction auxiliary. Suitable reaction auxiliaries are all customary inorganic or organic bases. These include, for example, alkaline earth metal hydroxides or alkali metal hydroxides, such as sodium hydroxide, calcium hydroxide, potassium hydroxide, or else ammonium hydroxide, alkali metal carbonates, such as sodium carbonate, potassium carbonate, potassium hydrogencarbonate, sodium hydrogencarbonate or ammoniumcarbonate, alkali metal acetates or alkaline earth metal acetates, such as sodium acetate, potassium acetate, calcium acetate or ammonium acetate, and also tertiary amines, such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

It is also possible to use a suitable excess of the amine of the formula (III), which is used as a reactant, to act simultaneously as reaction auxiliary.

When carrying out process (a) according to the invention the reaction temperatures can be varied within a substantial range. In general, the process is carried out at temperatures between 0° C. and +150° C., preferably at temperatures between +10° C. and +80° C.

To carry out process (a) according to the invention, 1.0 to 5.0 tool, preferably 1.0 to 2 tool of amine of the formula (III) and, if appropriate, 1.0 to 5.0 mol, preferably 1.0 to 2 tool of base as reaction auxiliary are generally employed per mole of activated (thio)carbonyltriazolinone of the formula (II). The reaction is carried out and the reaction products are worked up and isolated by known processes (compare, in this context, for example EP 283,876 or the preparation examples).

Suitable diluents for carrying out process (b) according to the invention are inert organic solvents. Solvents which are preferably used are those listed in the description of process (a) according to the invention.

If appropriate, process (b) according to the invention can be carried out in the presence of a suitable basic reaction auxiliary. Suitable reaction auxiliaries are all customary inorganic or organic bases. The following are preferably used: tertiary a mines, such as trimethylamine, triethylamine, tributylamine, N,N-dimethylaniline, pyridine, pipcridine, N-methylpiperidine, N,N-dimethylaminopyridine, diazabicyclooctane (DABCO), diazabicyclononene (DBN) or diazabicycloundecene (DBU).

However, an addition of such basic reaction auxiliaries is not essential.

When carrying out process (b) according to the invention, the reaction temperatures can be varied within a substantial range. In general, the process is carried out at temperatures between 0° C. and +150° C., preferably at temperatures between +40° C. and +120° C.

Process (b) according to the invention is usually carried out under atmospheric pressure. However, the process can also be carried out under increased or reduced pressure.

To carry out process (b) according to the invention, 1.0 to 5.0 mol, preferably 1.0 to 2.5 mol, of iso(thio)cyanate of the formula (V) and, if appropriate, 0.01 to 5.0 mol, preferably 0.1 to 2.5 mol, of base as reaction auxiliary are generally employed per mole of triazolinone of the formula (IV), which is unsubstituted in the 1-position.

The reaction is carried out and the reaction products are worked up and isolated by known processes (compare in this context, for example EP 283,876 or the preparation examples).

Acids which are suitable for carrying out process (c) according to the invention are all inorganic and organic acids which can usually be used for cleaving hydrazones. Inorganic mineral acids, such as hydrochloric acid, sulphuric acid and phosphoric acid, or acid ion exchangers, are preferably used.

Diluents which are suitable for carrying out process (c) according to the invention are all customary organic or inorganic solvents. Polar organic solvents which are miscible with water, in particular alcohols, such as methanol, ethanol, propanol or butanol, mixtures of these with water, or pure water, are preferably used as solvents.

When carrying out process (c) according to the invention, the reaction temperatures can be varied within a substantial range. In general, the process is carried out at temperatures between +20° C. and +150° C., preferably at temperatures between +50° C. and +120° C.

Process (c) according to the invention is usually carried out under atmospheric pressure or under reduced pressure. If the process is carried out under reduced pressure, then suitable pressure ranges are between 20 and 400 mbar, preferably between 100 and 200 mbar.

To carry out process (c) according to the invention, 1.0 to 5.0 mol, preferably 1.0 to 2.5 mol of acid are generally employed per mole of substituted triazolinone of the formula (Ia). The substituted triazolinone of the formula (Ia) is dissolved in a suitable amount of diluent, the required amount of acid is then added, and the mixture is slowly concentrated under reduced pressure in the course of several hours. In a particular embodiment, it is also possible to carry out process (c) according to the invention and the preparation of the precursors of the formula (Ia) required in one reaction step in a so-called "one-pot process". A procedure is followed in which either the activated (thio)carbonyltriazolinones of the formula (II) are selected as starting compounds, and these are then reacted in succession in the "one-pot process" with amines of the formula (III) in accordance with process (a) according to the invention and subsequently with acid in accordance with process (c) according to the invention, or, alternatively, the triazolinones of the formula (IV), which are unsubstituted in the 1-position are chosen as starting compounds and these are reacted in succession in the "one-pot process" with iso(thio)cyanates of the formula (V) in accordance with process (b) according to the invention and subsequently with acid in accordance with process (c) according to the invention.

Suitable diluents for carrying out process (d) according to the invention are inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, methyl t-butyl ether, methyl t-pentyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures of these with water or pure water.

If appropriate, process (d) according to the invention can be carried out in the presence of a suitable reaction auxiliary. Suitable reaction auxiliaries are customary inorganic or organic acids or bases. These include, for example, mineral acids, such as hydrochloric acid or sulphuric acid, carboxylic acids, such as acetic acid, sulphonic acids, such as p-toluenesulphonic acid, alkaline earth metal hydroxides, alkaline earth metal alcoholates, alkaline earth metal acetates, alkaline earth metal carbonates, alkaline earth metal hydrogencarbonates, alkali metal hydroxides, alkali metal alcoholates, alkali metal acetates, alkali metal carbonates or alkali metal hydrogencarbonates, such as, for example, sodium methylate, sodium ethylate, potassium tertbutylate, sodium hydroxide, potassium hydroxide, ammonium hydroxide, sodium acetate, potassium acetate, calcium acetate, ammonium acetate, sodium carbonate, potassium carbonate, potassium hydrogencarbonate, sodium hydrogencarbonate or ammonium carbonate, and also tertiary amines, such as trimethylamine, triethylamine, tributylamine, N,N-dimethylaniline, pyridine, piperidine N-methylpiperidine, N,N-dimethylaminopyridine, diazabicyclooctane (DABCO), diazabicyclononene (DBN) or diazabicycloundecene (DBU), or acid or basic ion exchangers.

When carrying out process (d) according to the invention, the reaction temperatures can be varied within a substantial range. In general, the process is carried out at temperatures between 50° C. and 200° C., preferably at temperatures between 80° C. and 180° C.

To carry out process (d) according to the invention, 0.01 to 2.0 mol, preferably 0.1 to 1.0 mol, of acid or basic reaction auxiliary are generally employed per mole of substituted triazolinone of the formula (Ib), if appropriate. The reaction is carried out and the reaction products are worked up and isolated in analogy to known processes (compare, in this context, for example Houben-Weyl "Methoden der organischen Chemie" [Methods in organic Chemistry], Volume XI, 1; P. 863, 867, 948; Thieme Verlag Stuttgart).

The reaction is carried out and the reaction products are worked up and isolated in each case in analogy to known processes (compare, in this context, for example EP 283, 876; EP 370,293 or the preparation examples).

The end products of the formula (I) are purified with the aid of customary processes, for example by column chromatography or by recrystallization.

They are characterized with the aid of the melting point or, in the case of compounds which do not crystallize, with the aid of the refractive index or proton nuclear resonance spectroscopy ($^1$H NMR).

The active compounds according to the invention can be used as defoliants, desiccants, agents for destroying broad-leaved plants and, especially, as weed-killers. By weeds, in the broadest sense, there are to be understood all plants which grown in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panictun, Digitaria, Phleum, Poa, Festuca, Eleusine, Brachiaria, Lolium, Bromus, Arena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Arena, Secale, Sorghum, Panicum, Saccharum, Ariahas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be employed particularly successfully for combating dicotyledon weeds and monocotyledon cultures, such as, for example, maize or wheat.

The active compounds can be converted into the customary formulations, such as solutions, emulsions, suspensions, powders, foams, pastes, granules, aerosols, natural and synthetic materials impregnated with active compound or very fine capsules in polymeric substances.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such has polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

When used as herbicides, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxapropethyl, fluazifopbutyl, haloxyfop-methyl and quizalofopethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuronmethyl, triasulfuron and tribenuron-methyl; thiocarbamates such as, for example, butylate, cycloate, diallate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

A mixture with other known active compounds, such as fungicides, insecticides, acaricides, nematicides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per hectare.

The preparation and the use of the active compounds according to the invention can be seen from the examples which follow.

PREPARATION EXAMPLES

EXAMPLE 1

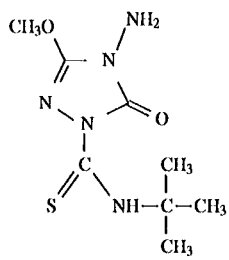

(Process a)

2.2 g (0.03 mol) of t-butylamine are added at room temperature, with stirring, to 2.7 g (0.01 mol) of 4-amino-3-methoxy-1-(phenoxy-thiocarbonyl)-1,2,4-triazolin-5-one in 100 ml of tetrahydrofuran, and, after the addition has ended, the mixture is stirred for 16 hours at reflux temperature. For work-up, the mixture is cooled to room temperature, precipitate which has separated out is filtered off, the filtrate is concentrated, and the residue is crystallized by trituration with diethyl ether.

1.8 g (74% of theory) of 4-amino-3-methoxy-1-[N-(2-methylprop- 2-yl) -amino]-carbonyl-1,2,4-triazolin-5-one of melting point 185° C. are obtained.

EXAMPLE 2

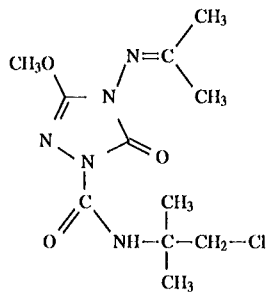

(Process b)

4.0 g (0.03 mol) of chloro-t-butyl isocyanate are added dropwise at room temperature, with stirring, to 2.55 g (0.015 mol) of 4-isopropylidenimino-3-methoxy-1,2,4-triazolin-5-one in 50 ml of acetonitrile, and, after the addition has ended, the mixture is stirred for 24 hours at room temperature. For work-up, precipitate which has separated out is filtered off with suction, washed with diethyl ether, dried and chromatoggraphed over silica gel (eluent: cyclohexane/ethyl acetate 1:3).

4 g (89% of theory) of 4-isopropylidenimino-3-methoxy- 1-[N-(3-chloro-2-methylprop-2-yl)-amino]-carbonyl-1,2,4-triazolin- 5-one are obtained as an oil.

$^1$H NMR (CDCl$_3$/tetramethylsilane): δ=7.85 ppm (NH).

EXAMPLE 3

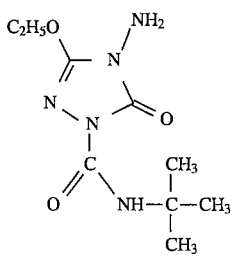

(Process b)

3.0 g (0.03 mol) of t-buryl isocyanate and 10 drops of diazabicycloundecene (DBU) are added dropwise at room temperature, with stirring, to 4.3 g (0.03 mol) of 4-amino-3-ethoxy-1,2,4-triazolin-5-one in 100 ml of acetonitrile, and, after the addition has ended, the mixture is stirred for 16 hours at room temperature. For work-up, the reaction mixture is concentrated in vacuum, and the residue is taken up in dichloromethane, washed with water until neutral, dried and concentrated in vacuum, and the residue is crystallized by trituration with diethyl ether.

2.7 g (37% of theory) of 4-amino-3-ethoxy-1-[N-(2-methylprop- 2-yl)-amino]-carbonyl-1,2,4-triazolin-5-one of melting point 124° C. are obtained.

EXAMPLE 4

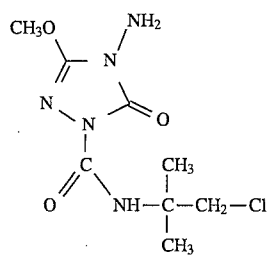

(Process c)

20 ml of water and 5 drops of dilute hydrochloric acid are added at room temperature, with stirring, to 3.5 g (0.0116 mol) of 4-isopropylideneimino-3-methoxy-1-[N-(chloro-t-butyl)-amino] -carbonyl-1,2,4-triazolin-5-one in 30 ml of ethanol, and the mixture is subsequently heated for 60 minutes at 40° C. and subsequently concentrated in vacuum, and the residue is purified by chromatography on silica gel (eluent:ethyl acetate).

1.8 g (59% of theory) of 4-amino-3-methoxy-1-[N-(3-chloro- 2-methylprop-2-yl)-amino]-carbonyl-1,2,4-triazolin- 5-one of melting point 118°–120° C. are obtained.

The following substituted triazolinones of the general formula (I)

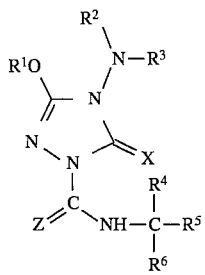

(I)

are obtained in an analogous manner and following the general preparation instructions:

| Ex. No. | $R^1$ | $R^2$ | $R^3$ | $R^4$ | $R^5$ | $R^6$ | X | Z | Physical Properties |
|---|---|---|---|---|---|---|---|---|---|
| 5 | $C_2H_5$ | H | H | $CH_3$ | $CH_3$ | $-CH_2-CH_2-C_6H_5$ | O | O | m.p. 103° C. |
| 6 | $C_2H_5$ | H | H | $CH_3$ | $CH_3$ | $-CH_2-Cl$ | O | O | m.p. 113° C. |
| 7 | $CH_3$ | H | H | $CH_3$ | $CH_3$ | $-CH_2-C_6H_5$ | O | O | m.p. 162° C. |
| 8 | $C_2H_5$ | H | H | $CH_3$ | $CH_3$ | $CH_3$ | O | S | m.p. 168° C. |
| 9 | $C_2H_5$ | H | H | $-(CH_2)_5-$ | | $CH_3$ | O | S | m.p. 144° C. |
| 10 | $CH_3$ | H | H | $CH_3$ | $CH_3$ | $CH_3$ | O | O | m.p. 115–118° C. |
| 11 | $CH_3$ | H | H | H | $CH_3$ | $C_6H_5$ | O | O | m.p. 85° C. |
| 12 | $CH_3$ | H | H | H | $CH_3$ | $-(CH_2)_2-\text{C}_6\text{H}_4-Cl$ | O | O | m.p. 108–110° C. |
| 13 | $CH_3$ | H | $-COOC_2H_5$ | $CH_3$ | $CH_3$ | $CH_3$ | O | O | m.p. 145° C. |
| 14 | $CH_3$ | $=C(CH_3)_2$ | | H | $CH_3$ | $C_6H_5$ | O | O | oil |
| 15 | $CH_3$ | $=C(CH_3)_2$ | | $CH_3$ | $CH_3$ | $CH_3$ | O | O | oil |
| 16 | $CH_3$ | $=C(CH_3)_2$ | | H | $CH_3$ | $-(CH_2)_2-\text{C}_6\text{H}_4-Cl$ | O | O | m.p. 67° C. |
| 17 | $CH_3$ | H | H | H | H | $t\text{-}C_4H_9$ | O | O | m.p. 96° C. |
| 18 | $CH_3$ | H | H | $CH_3$ | $CH_3$ | $C_2H_5$ | O | O | |

The following substituted triazolinones of the general formula (I)

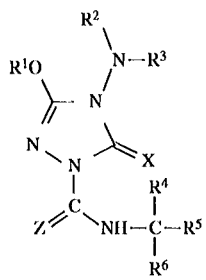

(I)

are obtained in an analogous manner and following the general preparation instructions:

| Ex. No. | $R^1$ | $R^2$ | $R^3$ | $R^4$ | $R^5$ | $R^6$ | X | Z | Physical Properties |
|---|---|---|---|---|---|---|---|---|---|
| 19 | $CH_3$ | H | H | H | H | $-CH_2-\langle\text{cyclohexyl}\rangle$ | O | O | |
| 20 | $CH_3$ | H | H | $-(CH_2)_5-$ | | $CH_3$ | O | O | |
| 21 | $CH_3$ | H | H | H | H | $-CH_2-\langle\text{C}_6\text{H}_4\rangle-C_2H_5$ | O | O | |
| 22 | $CH_3$ | H | H | H | $CH_3$ | $C_6H_5$ | O | O | |
| 23 | $CH_3$ | H | H | $CH_3$ | $CH_3$ | $-CH_2-CH_2-C_6H_5$ | O | O | m.p. 121° C. |
| 24 | $CH_3$ | H | H | H | $CH_3$ | $-CH_2-C_6H_5$ | O | O | m.p. 160° C. |
| 25 | $CH_3$ | H | H | H | $CH_3$ | $-\langle\text{cyclohexyl}\rangle$ | O | O | m.p. 118° C. (S configuration) |
| 26 | $CH_3$ | H | H | H | $CH_3$ | $n\text{-}C_4H_9$ | O | O | m.p. 97° C. |
| 27 | $CH_3$ | $=C(CH_3)_2$ | | $-CH_2-CH_2-CH-CH_2-CH_2-$<br>$\phantom{-CH_2-CH_2-}|$<br>$\phantom{-CH_2-CH_2-}CH_3$ | | H | O | O | (amorphous) |

*)The $^1$H NMR spectra were recorded in deuterochloroform ($CDCl_3$) or hexadeuterodimethylsulphoxide ($DMSO\text{-}d_6$) with tetramethylsilane (TMS) as the internal standard. The data given is the chemical shift as $\delta$ value in ppm.

PREPARATION OF THE STARTING COMPOUNDS

EXAMPLE II-1

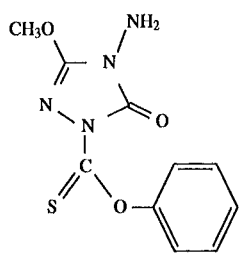

1.9 g (0.011 mol) of O-phenyl thiochloroformate are added dropwise at room temperature, with stirring, to 1.3 g (0.01 mol) of 4-amino-3-methoxy-1,2,4-trizolin-5-one in a mixture of 50 ml of dichloromethane, 50 ml of water, 0.5 g (0.0125 mol) of sodium hydroxide and 100 mg of tetrabutylammonium bromide, and the mixture is subsequently stirred for a further 15 hours at room temperature. For work-up, the organic phase is separated off, washed with dilute hydrochloric acid, dried and concentrated in vacuum and the residue is crystallized by trituration with ether/isopropanol (10:1).

0.5 g (19% of theory) of 4-amino-3-methoxy-1-phenoxythiocarbonyl-1,2,4-triazolin-5-one of melting point 158° C. is obtained.

The following activated (thio) carbonyltriazolinones of the formula (II)

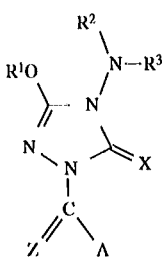

(II)

are obtained analogously and following the general preparation instructions.

| Ex. No. | $R^1$ | $R^2$ | $R^3$ | A | X | Z | Physical Properties |
|---|---|---|---|---|---|---|---|
| II-2 | $CH_3$ | H | H | $-O-C_6H_5$ | O | O | m.p. 161° C. |
| II-3 | $C_2H_5$ | H | H | $-O-C_6H_5$ | O | O | |
| II-4 | $C_2H_5$ | H | H | $-O-C_6H_5$ | O | S | |

EXAMPLE IV-1

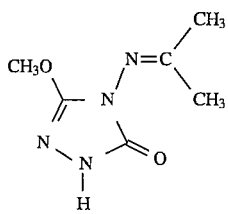

Catalytic amounts of p-toluenesulphonic acid are added to 13 g (0.1 mol) of 4-amino-3-methoxy-1,2,4-triazolin-5-one in 200 ml of acetone, and the mixture is subsequently refluxed for 12 hours, during which process an acetone/water mixture is continually distilled off. For work-up, the resulting solution is filtered while hot, the filtrate is subsequently concentrated in vacuum, and the residue is purified by chromatography on silica gel (eluent:acetone).

4 g (82% of theory) of 4-isopropylideneimino-3-methoxy- 1H-1,2,4-triazolin-5-one are obtained as an oil. $^1$H NMR (CDCl$_3$/tetramethylsilane): δ=9.7 ppm (NH).

EXAMPLE IV-2

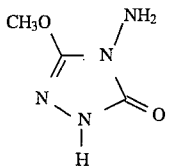

81.6 g (0.6 mol) of tetramethyl o-carbonate are added to 54 g (0.6 mol) of carbodihydrazide in 300 ml of methanol, and the mixture is subsequently stirred for 24 hours at room temperature and for a further 24 hours at reflux temperature. For work-up, the reaction mixture is cooled and concentrated in vacuum to one third of its volume, and the solid which has precipitated is filtered off, washed with diethyl ether and dried.

38 g (49% of theory) of 4-amino-3-methoxy-1H-1,2,4-triazolin- 5-one are obtained.

The following triazolinones of the general formula (IV)

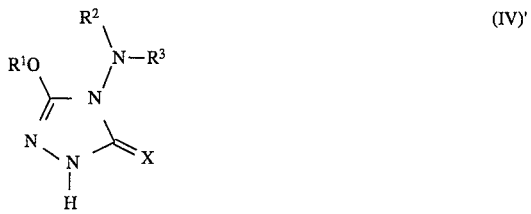

(IV)' which are unsubstituted in the 1-position, are obtained analogously following the general preparation instructions:

| Ex. No. | $R^1$ | $R^2$ | $R^3$ | X | Physical Properties |
|---|---|---|---|---|---|
| IV-3 | $CH_3$ | | $=CH-C_6H_5$ | O | m.p. 191° C. |
| IV-4 | $C_2H_5$ | | $=CH-C_6H_5$ | O | m.p. 204° C. |
| IV-5 | $CH_3$ | | $=CH-\phantom{x}C_6H_4-Cl$ | O | m.p. 207° C. |
| IV-6 | $C_2H_5$ | | $=CH-\phantom{x}C_6H_4-Cl$ | O | m.p. 240° C. |
| IV-7 | $CH_3$ | H | $-COO-C_2H_5$ | O | |
| IV-8 | $C_2H_5$ | H | H | O | m.p. 160–163° C. |
| IV-9 | $CH_3$ | H | $-COO-t-C_4H_9$ | O | |

USE EXAMPLES

In the use examples which follow, the compound given below was used as comparison substance:

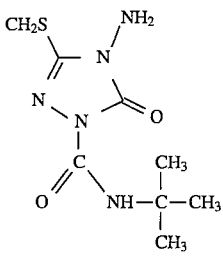

(A)

3-methylthio-4-amino-1-[N-(t-butyl)-aminocarbonyl]- 1,2,4-triazolin-5-one (disclosed in EP 391,187)

EXAMPLE A

Pre-emergence Test

Solvent: 5 parts by weight of acetone

Emulsifier: 1 part by weight of alkylaryl polyglycol ether

To produce a suitable preparation of active compound, one part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control.

The figures denote:

0%=no action (like untreated control)

100%=total destruction

In this test, a clearly superior activity combined with a similarly good crop plant selectivity compared with the prior art is shown, in this test, for example by the compound of preparation example 10.

EXAMPLE B

Post-emergence Test

Solvent: 5 parts by weight of acetone
Emulsifier: 1 part by weight of alkylaryl polyglycol ether To produce a suitable preparation of active compound, one part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen such that the particular amounts of active compound desired are applied in 2,000 l of water per hectare. After three weeks, the degree of damage to the plants is rated in % damage in comparison to the development of the untreated control.

The figures denote:

0%=no action (like untreated control)
100%=total destruction

In this test, a clearly superior activity combined with a similarly good crop plant selectivity compared with the prior art is shown, in this test, for example by the compound of preparation example 10.

It will be understood that the specification and examples are illustrative but not limitative of the present invention and that other embodiments within the spirit and scope of the invention will suggest themselves to those skilled in the art.

What is claimed is:

1. A substituted triazolinone of the formula

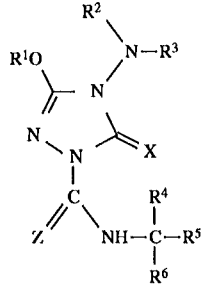

(I)

$R^1$ represents methyl or ethyl, $R^2$ and $R^3$ each independently of one another represent hydrogen or methyl, $R^4$ either represents hydrogen, cyano, methyl, ethyl, n- or i-propyl, n-, i-, s- or t-butyl, allyl, propargyl or straight-chain or branched halogenoalkyl having 1 to 6 carbon atoms and 1 to 13 identical or different halogen atoms, $R^5$ represents hydrogen, methyl, ethyl, n- or i-propyl, n-, i-, s- or t-butyl or straight-chain or branched halogenoalkyl having 1 to 6 carbon atoms and 1 to 13 identical or different halogen atoms or $R^4$ and $R^5$ together with the carbon atoms to which they are bonded represent cycloalkyl having 3 to 6 carbon atoms, $R^6$ represents hydrogen or straight-chain or branched alkyl having 1 to 7 carbon atoms which is optionally monosubstituted to trisubstituted by identical or different substituents wherein the substituents are selected from the group consisting of halogen, cyano, cycloalkyl having 3 to 6 carbon atoms, phenyl, phenoxy wherein said phenyl or phenoxy moieties are optionally monosubstituted to trisubstituted by identical or different substituents wherein the substituents are selected from the group consisting of fluorine, chlorine, bromine, cyano, methyl, ethyl, methoxy, ethoxy, trifluoromethyl, trifluoromethoxy and difluoromethoxy, $R^6$ furthermore represents phenyl which is monosubstituted to trisubstituted by identical or different substituents wherein the substituents are selected from the group consisting of fluorine, chlorine, bromine, cyano, nitro, methyl, ethyl, n- or i-propyl, methoxy, ethoxy, difluoromethyl, trifluoromethoxy or difluoromethoxy, X represents oxygen and Z represents oxygen and sulfur.

2. A substituted triazolinone according to claim 1 wherein $R^1$ represents methyl or ethyl, $R^4$ and $R^5$ each independently represents hydrogen or methyl, or together with each other and the carbon atoms from which they depend represent cyclohexyl, $R^6$ represents hydrogen, ethyl, butyl, chloromethyl, cyclohexylmethyl, phenyl, benzyl, phenethyl, chlorophenethyl or ethylbenzyl, and X represents O.

3. The substituted triazolinone according to claim 2, which has the formula

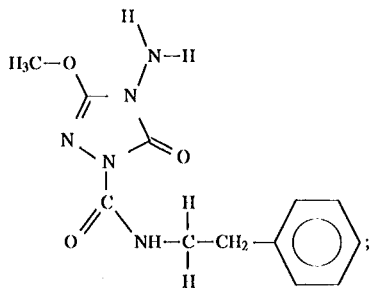

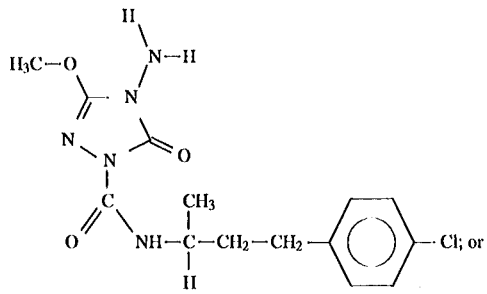

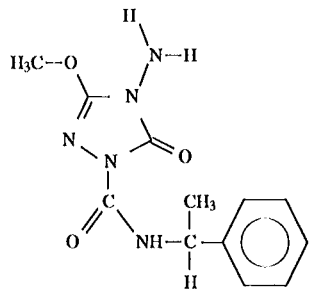

4. A substituted triazolinone of the general formula (I) according to claim 1 wherein such compound is 4-amino-3-methoxy-1-[-tert.butylamino] carbonyl-1,2,4-triazolin-5-one of the formula

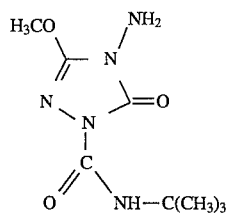

5. A herbicidal composition comprising a herbicidally effective amount of a compound according to claim 1 and a diluent.

6. A method of combating unwanted vegetation which comprises applying to such vegetation or to a locus from which it is desired to exclude such vegetation a herbicidally effective amount of a compound according to claim 1.

7. The method according to claim 6, wherein such compound is 4-amino-3-methoxy-1-[N-tert.butylamino]carbonyl- 1,2,4-triazolin-5-one.

* * * * *